(12) United States Patent
Veith et al.

(10) Patent No.: US 8,796,018 B2
(45) Date of Patent: *Aug. 5, 2014

(54) USE OF NANOPATTERNED SURFACES AND METHOD FOR ENRICHING OR ISOLATING CELLULAR SUBPOPULATIONS

(75) Inventors: Michael Veith, St. Ingbert (DE); Frank Narz, Witten (DE)

(73) Assignee: Leibniz-Institut fuer Neue Materialien Gemeinneutzige Gesellschaft mit beschraenkter Haftung, Saarbruecken (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/734,632

(22) PCT Filed: Nov. 7, 2008

(86) PCT No.: PCT/DE2008/001825
§ 371 (c)(1),
(2), (4) Date: Aug. 31, 2010

(87) PCT Pub. No.: WO2009/062470
PCT Pub. Date: May 22, 2009

(65) Prior Publication Data
US 2011/0014698 A1    Jan. 20, 2011

(30) Foreign Application Priority Data
Nov. 14, 2007   (DE) .......................... 10 2007 054 691

(51) Int. Cl.
| C12N 5/071 | (2010.01) |
| C12N 5/00 | (2006.01) |
| C12N 5/02 | (2006.01) |
| G01N 33/569 | (2006.01) |
| G01N 33/574 | (2006.01) |
| B82Y 30/00 | (2011.01) |

(52) U.S. Cl.
CPC .... G01N 33/57426 (2013.01); G01N 33/56966 (2013.01); B82Y 30/00 (2013.01)
USPC ...................................... 435/372.3; 435/325

(58) Field of Classification Search
CPC ............ B82Y 30/00; G01N 33/56966; C12Q 1/6816; C12N 5/06
See application file for complete search history.

(56) References Cited

U.S. PATENT DOCUMENTS

| 7,129,554 B2 * | 10/2006 | Lieber et al. ................... 257/414 |
| 7,956,339 B2 * | 6/2011 | Ohta et al. ............... 250/559.04 |
| 2005/0079591 A1 * | 4/2005 | Reich et al. ................ 435/173.1 |
| 2006/0014212 A1 * | 1/2006 | Benkovic et al. ............. 435/7.1 |
| 2009/0233349 A1 | 9/2009 | Petersen et al. |

FOREIGN PATENT DOCUMENTS

DE    10 2006 013 484        9/2007

OTHER PUBLICATIONS

Keon Woo Kwon et al., "Label-Free Microfluidic Separation of Human Breast Carcinoma and Epithelial Cells by Adhesion Difference," Solid-State Sensors, Actuators and Microsystems Conference, 2007, Transducers 2007. International, IEEE, Piscataway, NJ, Jun. 1, 2007, pp. 699-702, XP-031133286. (ISR).
Dewez, J.-L. et al., "Adhesion of mammalian cells to polymer surfaces: from physical chemistry of surfaces to selective adhesion on defined patterns," Biomaterials, Elsevier Science Publishers BV., Barking, GB, vol. 19, No. 16, Aug. 1, 1998, pp. 1441-1445, XP-004161407. (ISR).
Aronov et al., Hydroxyapatite nanoceramics: Basic physical properties and biointerface modification, Journal of the European Ceramic Society, Elsevier Science Publishers, Barking, Essex, GB, vol. 27, Nos. 13-15, Jan. 1, 2007, pp. 4181-4186, XP-022143719. (ISR).
G. Vona et al., "Isolation by Size of Epithelial Tumor Cells: A New Method of the Immunomorphological and Molecular Characterization of Circulating Tumor Cells," American Journal of Pathology, Jan. 2000, vol. 156, No. 1, pp. 57-63.
International Search Report for International Application No. PCT/DE2008/001825, Apr. 15, 2009, 2 pages.
Rosenberg et al., "*Comparison of Two Density Gradient Centrifugation Systems for the Enrichment of Disseminated Tumor Cells in Blood*," Cytometry 49, Wiley-Liss, Inc., 2002, pp. 150-158.
greiner bio-one, HEXAL Oncoquick, Instruction Manual, pp. 1-8, http://www.hexal-gentech.com/products/man_e.pdf, Jul. 2004.

* cited by examiner

*Primary Examiner* — Anne Gussow
*Assistant Examiner* — Channing S Mahatan
(74) *Attorney, Agent, or Firm* — Collard & Roe, P.C.

(57) ABSTRACT

The invention relates to the use of nanopatterned surfaces. It also relates to a method for enriching or isolating cellular subpopulations. To create a simple, versatile and specific method for enriching or isolating cellular subpopulations from a complex mixture, the invention proposes the use of nanopatterned surfaces for isolating and enriching cellular subpopulations from a complex mixture.

4 Claims, 3 Drawing Sheets

# USE OF NANOPATTERNED SURFACES AND METHOD FOR ENRICHING OR ISOLATING CELLULAR SUBPOPULATIONS

CROSS REFERENCE TO RELATED APPLICATIONS

This application is the National Stage of PCT/DE2008/001825 filed on Nov. 7, 2008, which claims priority under 35 U.S.C. §119 of German Application No. 10 2007 054 691.4 filed on Nov. 14, 2007. The international application under PCT article 21(2) was not published in English.

The invention relates to the use of nanopatterned surfaces. It also relates to a method for enriching or isolating cellular subpopulations.

Enriching or isolating cellular subpopulations from a complex mixture (e.g. T cells from blood) is an important step in pre-analytical sample preparation. It is currently done using antibodies directed against a specific surface protein and magnetic particles for separating the bound cells from the sample. This method, however, has the following drawbacks:

The cells in question must express a specific surface protein.
An antibody against this protein must be available.
Storing antibodies is problematic.
Antibodies are expensive.
When the antibody binds to the surface protein, the cell physiology may be changed.

Instead of magnetic-particle-based isolation, it is also possible to use fluorescent antibodies together with a FACS (fluorescence associated cell sorter). Here too, there is the problem of cost and, in addition, complex apparatus.

The use of physical parameters offers a further alternative, for example cell density (HEXAL Oncoquick) or cell size (*Am. J. Pathol.*, 2000, (1), 156, 57-63, *Isolation by Size of Epithelial Tumor Cells*, Giovanna Vona et. al.). However, as not every type of cell exhibits characteristic physical parameters, this approach is only possible if the cells in question do show characteristic physical parameters.

The object of the invention is to create a simple, versatile and specific method for enriching or isolating cellular subpopulations from a complex mixture.

This object is established according to the invention through use of nanopatterned surfaces for isolating and enriching cellular subpopulations from a complex mixture.

Surprisingly, it became apparent within the framework of the invention that specific cellular subpopulations adhere selectively and with hitherto unknown efficiency to nanopatterned surfaces of this kind—much better than to other substrates.

In a particularly preferred embodiment, these nanopatterned surfaces consist of one-dimensional nanowires of the kind described in DE 10 2006 013 484 A1. DE 10 2006 013 484 A1 relates to one-dimensional composite structures that contain at least one nanowire containing a metal core that is coated with a metal oxide. The metal oxide coating is preferably made of ceramics and the metal core is preferably a metal of the 3' main group of the period system of the elements. The nanowires consist of a metallic core surrounded by a ceramic shell, and are particularly suited for enriching or isolating cellular subpopulations from a complex mixture.

It is within the scope of the invention that the branched nanowires are one-dimensional composite structures having two dimensions in the sub-micrometer range, and that these composite structures are made up of a core of one material, particularly metal, and a shell of another material, particularly ceramic, and can be produced, as described in DE 10 2006 013 484 A1, by thermolytic decomposition of compounds of the general formula $El(OR)H_2$, where El stands for the elements Al, Ga, In and Tl
R stands for an alkyl (C3-C10) or a cycloalkyl (C5-C8) group It is within the scope of the invention that the cellular subpopulations are specific human or veterinary cells and that the complex mixture is plasma.

According to an embodiment of the invention, the plasma is human plasma.

A preferred embodiment of the invention consists in that the selectively adsorbed blood cells are intrinsically non-adherent cells, in particular Jurkat cells.

The term "intrinsically non-adherent cells" refers to cells that normally live in a suspension. As a rule, growing cells of this kind on a substrate is extremely difficult.

The scope of the invention also includes a method for enriching or isolating cellular subpopulations, the cellular subpopulations being enriched on nanopatterned surfaces.

In a particularly preferred embodiment, the nanopatterned surfaces are made up of one-dimensional nanowires of the kind described in DE 10 2006 013 484 A1 and consisting of a metallic core surrounded by a ceramic shell. Cells adhere selectively to these wires, thus becoming enriched.

It is within the scope of the invention that the cellular subpopulations are specific blood cells, and that the complex mixture is plasma.

It is within the scope of the invention that the plasma is human plasma.

According to the invention, ultimately, the cellular subpopulations are intrinsically non-adherent cells, in particular Jurkat cells.

The invention is described below in more detail and in non-restrictive manner on the basis of tests. The experimental results are shown in the drawings.

Figure 1A:
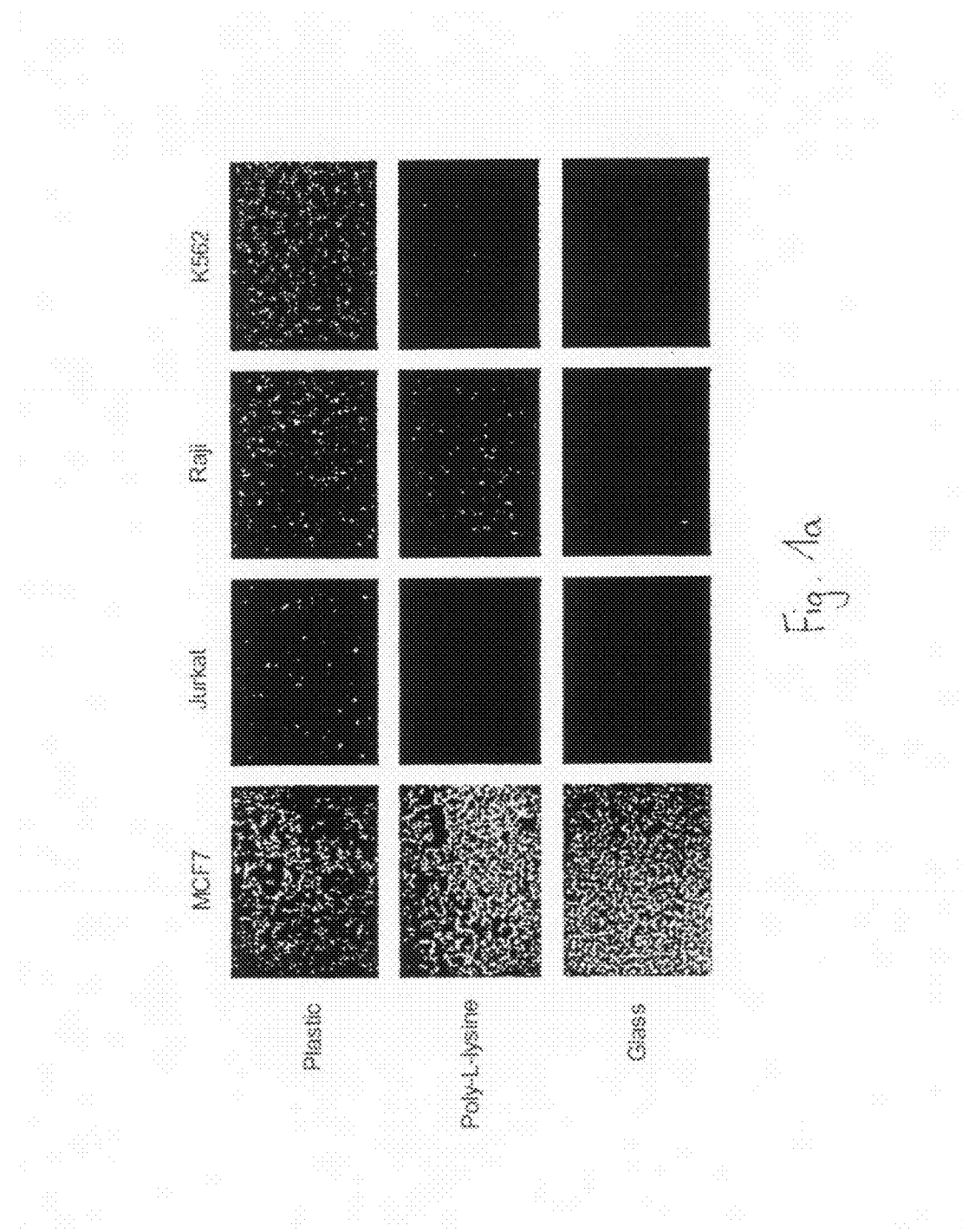
FIG. 1a and FIG. 1b show fluorescence micrographs of various cell cultures on different substrates and after trypsination.

The growth of eukaryotic cells was observed on watch glasses that are coated with one-dimensional composite structures in the submicrometer range and have a core made of one material and a shell made of another material.

Use was made of circular watch glasses (Menzel watch glasses, Germany, No. CB00120RA1, 12 mm diameter, 0.13-0.16 mm thickness, batch No. 4710486).

Some of these watch glasses were coated with a one-dimensional composite structure based on $Al/Al_2O_3$, as described in DE 10 2006 013 484 A1.

To remove impurities, both the coated and the uncoated watch glasses were treated as follows:

The watch glasses (the coated ones with the coated side facing upwards) are placed in the wells of a 24-well cell culture plate.
500 µl 70% ethanol are added and left for 5 min in the watch glasses.
The watch glasses are rinsed 3 times with sterile water, using 500 µl water each time.
The watch glasses are rinsed 3 times with sterile PBS (phosphate-buffered saline solution), using 500 µl of PBS each time.

Use was made of watch glasses coated with sterile polylysine (BD Sciences, 352085) and of uncoated watch glasses. The former were only washed. In addition, cells were cultivated directly in the 24-well cell culture plates, without watch glasses.

Cells of a suitable density (typically $4-8 \cdot 10^4$ cells per well) were introduced into 1 ml serum containing cell culture medium and cultivated at 37° C. with 5% $CO_2$ and 100% relative humidity.

The cells were cultivated for up to 72 h and inspected daily with a light-optical microscope. Subsequently, non-adhering cells were washed off by rinsing the wells and watch glasses twice with 1000 µl PBS. The remaining, adherent cells were fixed by adding 500 µl 100% ethanol (5 minutes at RT). Following removal of the ethanol, the cell nuclei were stained by adding 500 µl Hoechst 33342 (Invitrogen, 0.1% in PBS). Micrographs were produced with a fluorescence microscope.

The following test series was carried out:

Test

In this test (07D.0031 pp 38; CK), Jurkat cells (human T cell line in suspension), Raji cells (human macrophage cell line in suspension), K562 cells (human B cell line in suspension) and MCF7 cells (adherent human breast cancer cell line) were cultivated on watch glasses made of plastic (designation in FIG. 1a: Plastic), on watch glasses coated with poly-L-lysine (designation in FIGS. 1a and 1b: Poly-L-lysine), on watch glasses made of glass and on watch glasses coated with $Al/Al_2O_3$ (designation in FIG. 1b: Al/AlO).

After 24 h, the cells were washed off and the cell nuclei stained without the cells having been fixed with ethanol. Micrographs were prepared and the cells detached by adding a trypsin/EDTA solution (designation in FIG. 1b: after T/E) (Invitrogen). The remaining cells were washed with PBS and photographed again. In this test, the enhanced adherence of Jurkat cells (as an example of intrinsically non-adherent cells) on the $Al/AlO_x$ coating was observed. It was possible to detach the adhering cells alive from the coating by means of trypsination, indicating that protein is involved in the adherence mechanism.

Figure 1B:
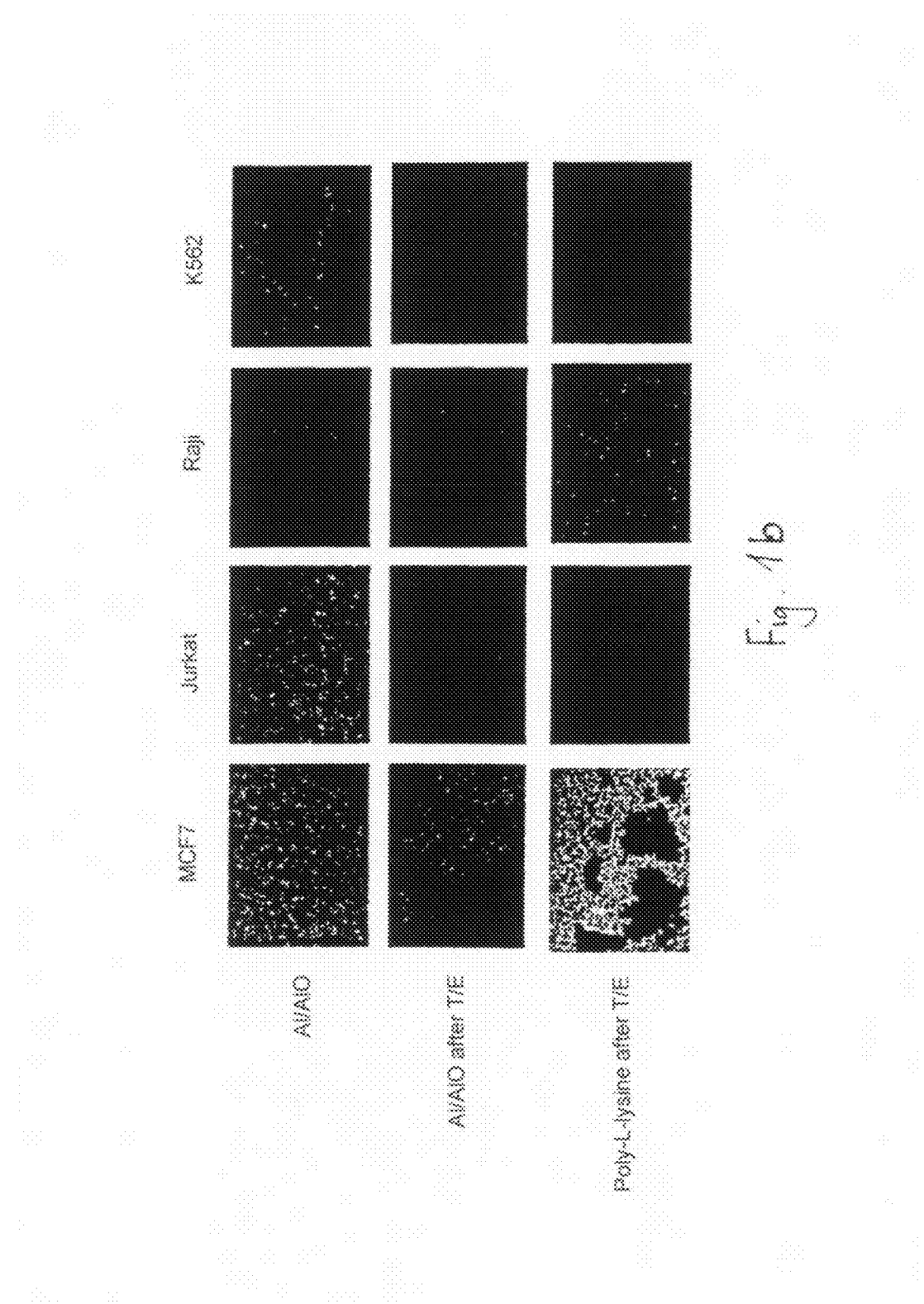

The fluorescence micrographs shown in FIGS. 1a and 1b show that the intensity of the fluorescence is somewhat less with the $Al/AlO_x$-coated watch glasses because the coating absorbs light. Despite this, it is evident that intrinsically non-adherent cells, too, such as Jurkat cells, are enriched much more efficiently on $Al/AlO_x$-coated watch glasses than on the other substrates, and, as shown in further tests, survive in fully functional form over longer periods (more than 72 h). The fact that these cells can be detached alive (and thus cultivated and processed further) means that even minute quantities of such cells can be cyclically enriched on this substrate. Furthermore, cell division is uniform and not too dense, making it easy to observe the cell morphology microscopically, for example, and thus to determine the stage.

Adherence and growth of intrinsically adherent cell lines such as MCF7 is not disturbed by the $Al/AlO_x$ coating.

Figure 2:
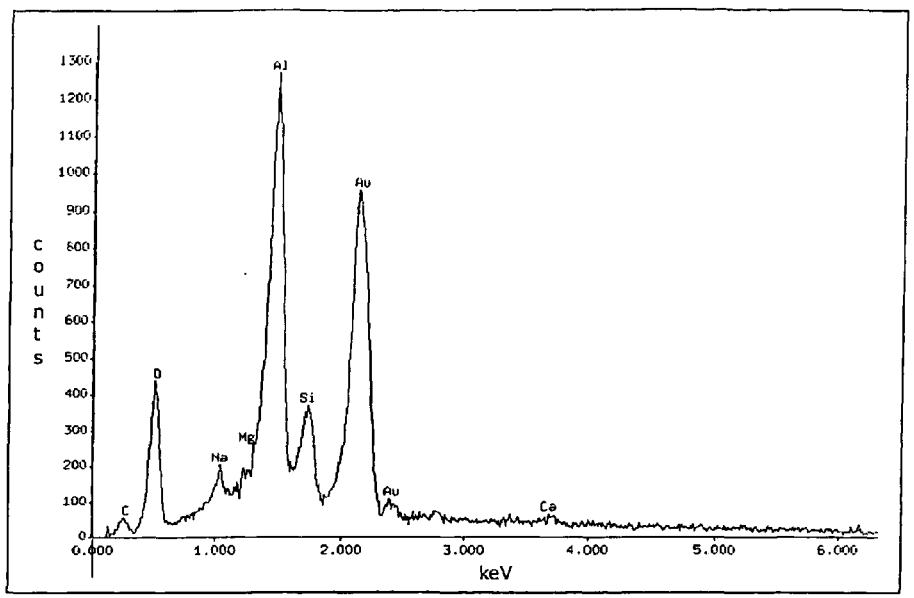
FIG. 2 shows an EDX micrograph of the nanopatterned surface according to the invention.

The EDX micrograph (FIG. 2) of the nanopatterned surface according to the invention shows that it does not contain significant amounts of carbon and can thus be considered an inorganic substrate.

The invention claimed is:

1. A method for enriching or isolating Jurkat cells from a complex mixture of cellular subpopulations, the method comprising a step of:
enriching the cellular subpopulations cyclically by detaching cells alive and cultivating and further processing them on nanopatterned surfaces, said cellular subpopulations being intrinsically non-adherent cells and said nanopatterned surfaces being made up of one-dimensional nanowires comprising a metallic core surrounded by a ceramic shell, have two dimensions in the sub-micrometer range and are produced by thermolytic decomposition of compounds having the general formula $El(OR)H_2$, where El stands for the elements Al, Ga, In and Ti and R for an alkyl (C3-C10) or a cycloalkyl (C5-C8) group.

2. The method according to claim 1, wherein the cellular subpopulations are blood cells;
wherein the enriching of the cellular subpopulations on the nanopatterned surfaces occurs from a complex mixture; and
wherein the complex mixture is plasma.

3. The method according to claim 2, wherein the plasma is human plasma.

4. The method according to claim 1, wherein the cellular subpopulations are Jurkat cells.

* * * * *